United States Patent [19]

Mroz et al.

[11] 4,231,370
[45] Nov. 4, 1980

[54] DISPOSABLE DIAPER TYPE GARMENT HAVING WETNESS INDICATOR

[75] Inventors: Judith C. Mroz; Dennis A. Thomas, both of Cincinnati, Ohio

[73] Assignee: The Procter & Gamble Company, Cincinnati, Ohio

[21] Appl. No.: 50,013

[22] Filed: Jun. 18, 1979

[51] Int. Cl.³ .............................................. A61F 13/16
[52] U.S. Cl. .................................... 128/287; 116/206
[58] Field of Search ............... 128/284, 286, 287, 290, 128/296, 156, 771; 116/206

[56] References Cited

U.S. PATENT DOCUMENTS

| | | | |
|---|---|---|---|
| 3,731,685 | 5/1973 | Eidus | 128/284 |
| 3,759,261 | 9/1973 | Wang | 128/287 |
| 3,918,433 | 11/1975 | Fuisz | 128/284 |
| 3,918,454 | 11/1975 | Korodi et al. | 128/284 |
| 3,952,746 | 4/1976 | Summers | 128/284 |
| 4,192,311 | 3/1980 | Felfoldi | 128/287 |

FOREIGN PATENT DOCUMENTS

| | | | |
|---|---|---|---|
| 678754 | 1/1964 | Canada | 128/284 |
| 2031104 | 12/1971 | Fed. Rep. of Germany | 128/771 |

*Primary Examiner*—C. Fred Rosenbaum
*Attorney, Agent, or Firm*—Thomas J. Slone; Fredrick H. Braun; Richard C. Witte

[57] ABSTRACT

An improved absorbent product, such as a disposable diaper type garment having a wetness indicator disposed between a translucent cover member and an absorbent member. The improvement relates to providing a flexible pH-change/color-change wetness indicator coating on a surface portion of the product which is visible through the cover member, and which retains sharp edge definition of the coated surface portion when wetted; for instance, by urine. The coating is preferably applied in the form of a stripe to a portion of the inwardly facing surface of a backsheet of a disposable diaper. Such a coating comprises a solid-solid mixture (e.g., solution) of a pH-change/color-change type material dispersed in a matrix of adhesive material which coating is sufficiently flexible to not substantially impair the flexibility of the product, and which coating is sufficiently adhesive and flexible to remain on the coated surface portion through a normal period of use of the product.

7 Claims, 4 Drawing Figures

WETNESS INDICATOR COATING THICKNESS
VS.
COLOR CHANGE TIME
(URINE pH 6.3)

DISPOSABLE DIAPER TYPE GARMENT HAVING WETNESS INDICATOR

DESCRIPTION

Technical Field

This invention relates to absorbent products such as disposable diapers and the like which are provided with wetness indicators.

Background Art

U.S. Pat. No. 4,022,211 which issued May 10, 1977 to Terry K. Timmons et al. discloses a Wetness Indicator For Absorbent Pads which indicator comprises a water-soluble or water-dispersible coloring agent. The coloring agent may be applied, for instance, in a printed pattern on the inwardly facing surface of a light-transmitting, fluid-impervious backing sheet of a disposable diaper. Then, when the diaper is wetted, the coloring agent becomes invisible. The coloring agent may be used by itself, or with a suitable binder, or with a separate carrier means such as an abosrbent sheet. A preferred form of coloring agent is said to be a water-soluble dye in a water-soluble polyvinyl alcohol binder.

U.S. Pat. No. 3,675,654 which issued July 11, 1972 to Joseph S. Baker et al. discloses a Disposable Article With Moisture-Actuated Indicating Agent. The indicating agent is stated to comprise either a small amount of finely divided water soluble dye having a high dye strength or such a dye admixed with a finely divided diluent masking agent, such as talcum powder. When wetted, the dye is dissolved, and the dye solution becomes visible through a translucent backsheet of the article. Such a solution in combination with an absorbent member substantially obviates producing a sharply defined pattern of activated wetness indicator.

U.S. Pat. No. 3,731,685 which issued May 8, 1973 to William Eidus discloses a Moisture Indicating Strip For Diapers and Surgical Dressings. Essentially, one end portion of an indicator strip is secured to such a garment so that the opposite end extends beyond an edge of the garment, and so that the attached end is disposed to become wet when the garment is wetted in use. The strip is capable of supporting capillary action from the secured end to the opposite end which opposite end is impregnated with a chemical which changes color when wet.

U.S. Pat. No. 3,952,746 which issued Apr. 27, 1976 to F. Wayne Summers discloses a Humidity Indicating Diaper Cover which, essentially, comprises a moisture indicator strip and means for moisture activating and viewing the indicator strip during the use of the diaper.

U.S. Pat. No. 3,063,812 which issued Nov. 13, 1962 to Galen F. Collins discloses a Determination of Albumin In Liquids; in particular albumin in urine. Basically, the basis of the invention is stated to be "protein error" exhibited by certain indicators whereby in solutions containing protein such indicators undergo their characteristic acid-to-base color change at a lower pH value than that at which they would change color in the absence of protein. For instance, an indicator tablet comprising bromophenol blue is provided with an acid reacting substance to lower the pH value of urine below the acid-to-base color change point of the indicator. Then, if the color change occurs it indicates the presence of albumin in the urine.

U.S. Pat. No. 3,004,895 which issued Oct. 17, 1961 to S. M. Schwartz discloses a Diaper Rash Preventative which, essentially, comprises a member which is readily permeable by ammonia and means for immobilizing ammonia which passes therethrough. Thus, when the permeable member is a wall portion of a pouch containing an ammonia immobilizing agent, the pouch can be disposed inside a diaper or diaper pail and be effective with respect to immobilizing ammonia which contacts the pouch as, for instance, when a diaper is wetted with urine. Such a pouch may, if translucent, further contain a pH-change/color-change indicator for the purpose of visibly indicating when the effectiveness of the ammonia immobilizing agent has been exhausted.

U.S. Pat. No. 2,537,124 which issued Jan. 9, 1951 to Roland D. Earle et al. disclose a Latex Adhesive Containing Phenolphthalein and Method of Using Same. This patent teaches the use of a pH-change/color change indicator in a latex-type adhesive which will undergo a visible color change as the adhesive dries. A user of the adhesive can then infer the degree of adhesive dryness from the color of the adhesive and, based thereon, decide when to bring adhesive coated articles together for the purpose of adhesively securing them together. Thus, this patent discloses a degree of dryness indicator which is visible prior to its end use but which is not disclosed to be visible after its intended use. Neither does this patent suggest that the adhesive need be flexible when dry, nor that its color change would reverse if rewetted. Indeed, as disclosed, the aqueous phase of the adhesive would have a pH of at least nine (9) and be reduced upon drying. It is believed that such a high pH indicator would not, after undergoing a color change upon drying, reverse its color change when rewetted with urine.

As compared to the foregoing background art, the present invention provides a visible pH-change/color-change wetness/urine indicator coating which obviates the need for a discrete substrate with its attendant application complexities of cutting, registration, and securement; and which comprises means for substantially obviating migration of colorant when wetted. Thus, the resulting color indicating pattern of a coating embodiment of the present invention will have a sharp edge definition when wetted rather than a quasi blurred edge definition such as would result from high dye strength materials which are relatively highly water-soluble. Also, the present invention substantially obviates migration of colorants through an adjacent absorbent member and thereby reduces the likelihood of skin irritations which might otherwise be precipitated.

DISCLOSURE OF THE INVENTION

In accordance with one aspect of the present invention, there is provided an improved disposable absorbent product having a pH-change/color-change wetness indicator. The wetness indicator is a coating material which comprises a solid-solid dispersion of a pH-change/color-change material which coating is sufficiently flexible to not substantially impair the flexibility of the product, and which coating is sufficiently flexible and adhesive to remain on an associated coated surface portion of the product during the normal use of the product. The coating is applied to a surface portion of the product so that it is visible from the outside to, for example, an attendant of the person using the article. Preferably, the coated surface is a patterned portion of the inwardly facing surface of a translucent cover member of the article; for instance, a water-impervious thermoplastic backsheet of a disposable diaper.

BRIEF DESCRIPTION OF THE DRAWINGS

While the claims hereof particularly point out and distinctly claim the subject matter regarded as forming the present invention, it is believed the invention will be better understood from the following description of the invention taken in conjunction with the accompanying drawings in which corresponding features of the two views are identically designated, and in which:

DETAILED DESCRIPTION OF THE INVENTION

Figure 1:
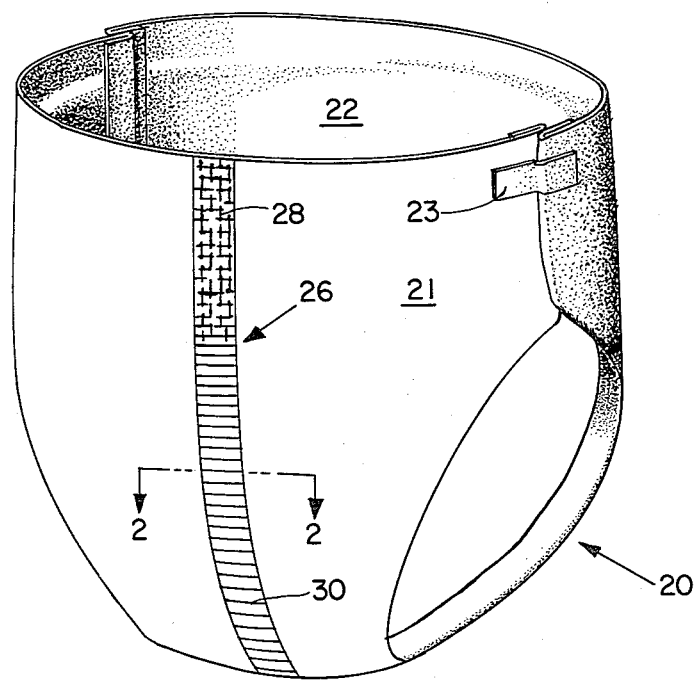
FIG. 1 is a perspective view of a disposable diaper embodying the present wetness indicator invention, and in which view a stripe of pH-change/color-change coating material is shown to be partially activated.
Figure 2:
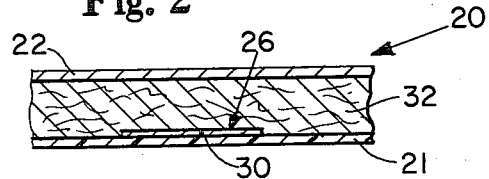
FIG. 2 is an enlarged scale fragmentary sectional view taken along line 2—2 of FIG. 1.

An exemplary improved disposable diaper 20 embodying the present invention is shown in perspective in FIG. 1 and in the fragmentary sectional view FIG. 2. Diaper 20 comprises a moisture impervious cover member or backsheet 21, a moisture pervious topsheet 22, tape fasteners 23 of which there are two but only one shown in FIG. 1, and moisture indicator coating 26 which is coated onto a portion of the inwardly facing surface of backsheet 21. Portion 28 of coating 26 represents an unactivated portion of coating 26, and portion 30 represents an activated portion of coating 26. Diaper 20 further comprises an absorbent member or core 32 as shown in FIG. 2.

The components and materials of diaper 20 are very flexible so that the diaper will be sufficiently compliant to conform to the shape of the lower torso of the wearer during the period of use of the diaper. For instance, backsheet 21 is preferably a thin (eg., 1 mil) translucent polyethylene film; the topsheet 22 is preferably a thin, flexible sheet of moisture pervious hydrophobic material; and the absorbent core 32 is preferably an air-laid web of absorbent fibrous material.

Briefly, the present invention is an improved diaper type garment which is very flexible for the above stated reasons, and which garment includes a highly flexible pH-change/color-change wetness indicator coating so disposed that it will be activated within a relatively short time after the wearer urinates. More specifically, the present invention provides an acid buffered pH-change/color-change coating material which, when wetted with urine, will undergo a substantial color change; and which coating is so disposed that the color change will be visible to, for instance, a percipient attendant of the wearer. Thus, while the stripe of coating 26 of diaper 20 is said to be applied to the inside surface of backsheet 21, it is not intended to thereby limit the present invention. Rather, such a coating could also be applied, for instance, to the outwardly facing surface of absorbent core 32.

Coating 26 is a solid-solid mixture, for instance, a solid-solid solution of a pH-change/color-change type material dispersed in a matrix of adhesive material. The matrix material is preferably sufficiently flexible so that the coating 26 does not substantially impair the flexibility of a disposable diaper or other product in which it is incorporated. Moreover, the coating must be sufficiently adhesive and flexible to remain intact on the surface coated therewith through a normal period of use. That is, coating 26 is highly flexible with respect to the other components of diaper 20 so that the coating will not substantially impair the flexibility or conformability of the diaper.

An exemplary coating 26, as described hereinabove and as shown in FIGS. 1 and 2, may be formed from a coating composition comprising four principle functional components:

a first latex composition in the amount of about 33%;

a second latex composition in the amount of about 66%;

an acid buffer such as phosphoric acid in the amount of about 1%; and, a pH-change/color-change material such as bromophenol blue in the amount of about 0.07%.

The first latex (Latex 1) composition of the above described exemplary coating composition is an aqueous emulsion copolymer of styrene, and 2-ethylhexyl acrylate with less than 5% methacrylate acid and less than 5% n-methylol acrylamide. The ratio of the styrene and 2-ethylhexyl acrylate is adjusted to yield a random copolymer with a glass transition temperature, Tg of about $-18°$ C. The first latex has an intrinsic viscosity of about 1.4 measured in tetrahydrofuran at 25° C. Distilled water exhibits a contact angle of from about 74° to about 80° with a dry coating of this latex after about 60 seconds of contact.

The second latex (Latex 2) composition of the above described exemplary coatingcomposition is preferably product No. X695-385-04 which is a product of Findley Adhesives, Inc., Milwaukee, Wisconsin. That product has the following components:

30.49%: Airflex 405, Air Products & Chemicals Inc., Allentown, PA (A non-ionic surfactant stabilized, random vinyl acetate-ethylene copolymer emulsion).

7.53%: Product Flx-0012, Pearsall Chemical Corp., Houston, TX (A liquid chlorinated paraffin).

60.98%: Plyamul 40-140, Reichhold Chemical Corp., White Plains, NY (An alcohol stabilized, random homo-polymer polyvinyl acetate emulsion).

0.05%: Colloids 681-F, Colloids Inc., 394 Frelinghuysen Ave., Newark, NJ (A defoamer).

0.25%: Drexoil 110 defoamer, Lubricants, Inc., P.O. Box 21, Pewaulkee, WI (A defoamer).

0.7—1.0%: Phosphoric acid (75% by weight), Fisher Scientific Co., Fairtown, NJ (The amount of phosphoric acid is determined by the pH of the mixture, acid is added to make the pH=1.0).

These components are mixed in the following manner. The Airflex 405 is placed in a compounding vessel and, under high agitation, the chlorinated paraffin is added and mixing is continued for about 45 minutes. After the chlorinated paraffin has been thoroughly dispersed, Colloids 681-F defoamer is added to the compounding vessel, mixed with the other materials therein, and the Drexoil 110 defoamer is mixed thereinto. The phosphoric acid is premixed with ¼ as much water in a separate vessel and after mixing, is added to the compounding vessel. This is followed by the addition of the Plyamul 40-140 with good agitation. The entire composition is stirred for 45 minutes until smooth. The pH of the composition is adjusted to about 1.0 by addition of a premix of phosphoric acid with water. The viscosity of the product is adjusted to from about 750 to about 1500 C. cps at 25° C. by water addition, using a Brookfield Viscometer Model RPT, spindle #5 at 20 rpm. Distilled water exhibits a contact angle of from about 5° to about 11° with a dry coating of this latex composition after about 60 seconds of contact.

The components of the exemplary coating mix described hereinabove are combined in the following preferred manner:
the bromophenol blue is slowly and with mixing added to and dissolved in Latex 1 to form a mixture A;
the phosphoric acid is then slowly and with mixing added to the mixture A to form a mixture B; and
Latex 2 is then added to the mixture B.

This resultant aqueous mixture can then be applied to the inside of the thermoplastic backsheet of a diaper. This indicator solution will adhere to the polyethylene of the backsheet and dry to a flexbile coating that is light yellow in color. Distilled water exhibits a contact angle of 7°—10° with the dry film of this example mixture. (Contact angle is measured after 60 seconds of contact). When urine migrates through the absorbent material of the diaper and wets the indicator stripe, the color of the indicator will change from light yellow to blue. With the above mixture and urine of a pH of 6.2 this color change will occur within 5 minutes. Lower pH urines will cause longer change times and higher pH urine will cause shorter change times; reference FIG. 3.

Figure 4:
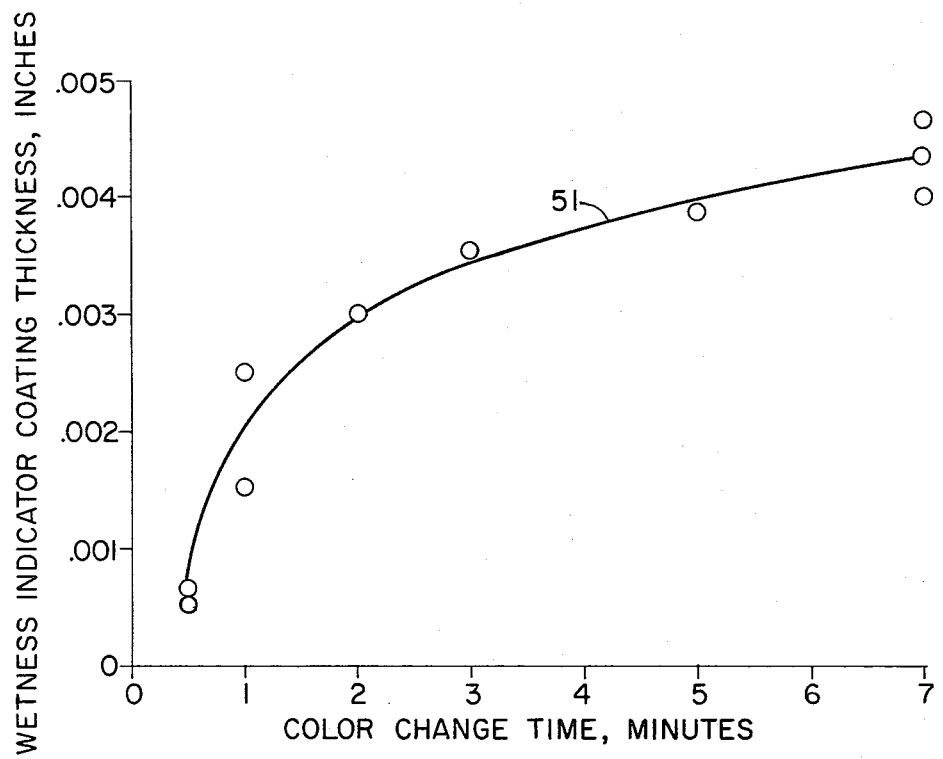
FIG. 4 is a graph showing the relation between the thickness of a color indicator coating and the time to achieve a predetermined degree of color change when the coating is activated by urine having a pH of 6.3

Further, the color change time can be affected by the thickness of the indicator film; reference FIG. 4. The preferred dry film thickness for the exemplary coating material described above is about 0.0015 inches.

After the indicator has changed color, it will remain reasonably immobilized in the matrix, and will therefore, remain a wetness signal for sometime after color change. It is believed that the latex matrix provides both a physical barrier to the migration of the large bromophenol blue molecules and physical protection from the fluid flow patterns within the diaper.

The above formulation can be varied to adjust the indicator properties. If the above ratio of Latex 1, with which distilled water exhibits a contact angle of 74°—80°, to Latex 2, with which distilled water has a contact angle of 5°—11°, is varied the time required for indicator developments and efficiency of retaining the bromophenol blue are affected. For example, if the ratio of Latex 1:Latex 2 (described above as 1:2) were changed to 1:1 the resultant indicator would change color more quickly, but would hold bromophenol blue less strongly and bleeding of the color would occur. If the same ratio were changed to 1:4, the resulting indicator would change color more slowly, and would hold bromophenol blue more strongly.

The exemplary coating composition is preferably applied in a predetermined pattern; for instance, a one-half-inch wide stripe having a thickness of about one-and-one-half mils such as stripe 26, FIG. 1. Then, upon color change, the edge definition of the pattern remains sharp because migration of the bromophenol blue is substantially obviated by the acid buffered latex matrix.

Figure 3:
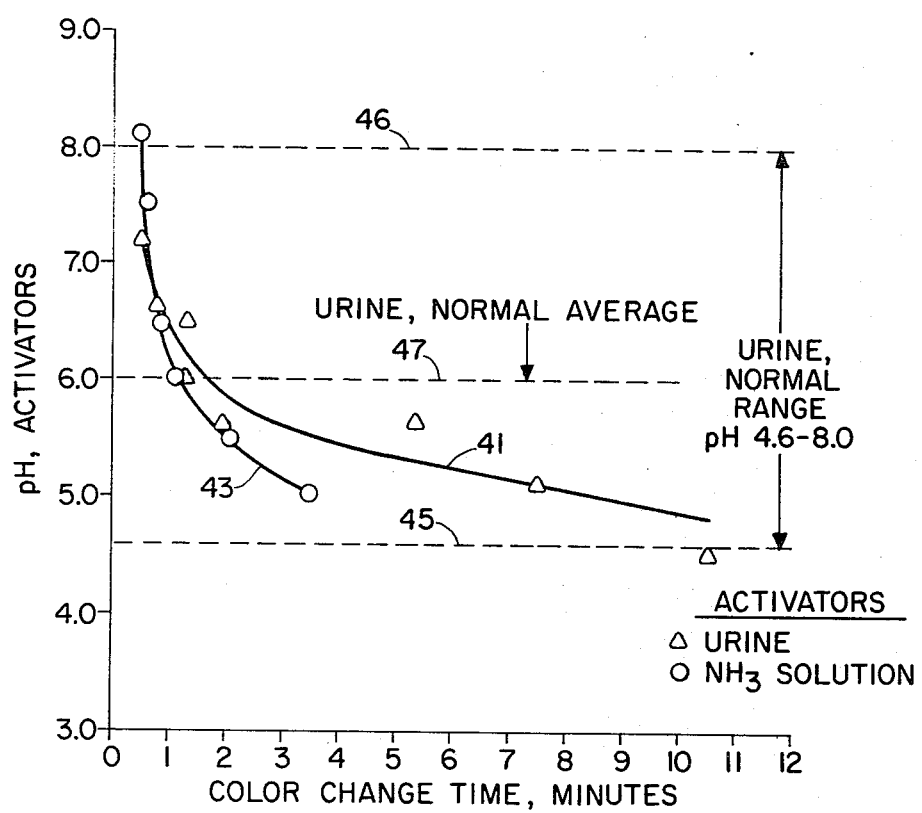
FIG. 3 is a graph showing the relation between the pH of two color-change activators and the time to effect a substantial color change of a wetness indicator coating of an embodiment of the present invention.

FIG. 3 is a graph of activator pH versus color-change-time data which was obtained by wetting a number of exemplary disposable diapers embodying the present invention. The stripe 26 of each diaper had a thickness of one-and-one-half mils; was one-half-inch wide; and extended generally vertically along the medial posterior portion of the inner surface of the diapers' backsheets. Curve 41, FIG. 3, was derived from samples activated by urine, and Curve 43 was derived from samples activated by ammonia. Lines 45 and 46 represent the low and high pH values, respectively, of the normal range of urine as reported on page 13 in *Interpretation of Diagnostic Tests*, A Handbook Synopsis of Laboratory Medicine, Copyrighted 1970 by Little, Brown and Company (Inc.), which handbook is further identified by Library Of Congress Catalog Card No. 72-112015. Line 47 on FIG. 3 identifies the pH value of normal average urine as also reported in the above identified handbook.

FIG. 4 is a graph (Curve 51) of wetness indicator coating 26 thicknesses versus color change times which data were obtained through the use of sample disposable diapers wherein coatings 26 comprised the exemplary coating composition described hereinabove, and all the samples were activated by urine having a pH of about 6.3.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of this invention.

What is claimed is:

1. An improved disposable diaper type garment having a wetness indicator disposed intermediate a flexible translucent cover member and a flexible absorbent member, said improvement comprising a flexible pH-change/color-change type wetness indicator coating which is so disposed on an area of a said member that it is visible through said cover member and is in liquid communicable relation with said absorbent member, said coating comprising a solid-solid mixture of a pH-change/color-change type material dispersed in a highly flexible matrix of adhesive material.

2. The improved disposable diaper type garment of claim 1 wherein said pH-change/color-change material comprises bromophenol blue, said matrix of adhesive material comprises a highly flexible latex adhesive, and said coating comprises sufficient acid buffering means for providing said coating with an initial pH of less than about 3.0

3. The improved disposable diaper type garment of claim 2 werein said coating comprises sufficient said acid buffering means for substantially obviating color change of said coating due to atmospheric moisture.

4. The improved disposable diaper type garment of claim 2 or 3 wherein said mixture is a solid-solid solution, and wherein said latex adhesive is sufficiently hydrophilic to enable some portion of said bromophenol blue to be contacted by urine contacting said coating, and said coating comprises means for sufficiently obviating migration of said bromophenol blue in said matrix that said bromophenol blue will not be substantially dispersed into contacting urine adjacent said coating whereby the as-applied edge definition of said coating will remain substantially intact when said coating undergoes a urine activated, pH-change induced color change.

5. The improved disposable diaper type garment of claim 4 further comprising sufficient said acid buffering means for providing said coating with an initial pH of from about 1.0 to about 2.0.

6. The improved disposable diaper tye garment of claim 5 wherein said acid buffering means comprises phosphoric acid.

7. The improved disposable diaper type garment of claim 5 wherein said cover member is a sheet of translucent thermoplastic material, said coating is disposed on a portion of an inwardly facing surface of said cover member, and said coating comprises sufficient bromophenol blue and said acid buffering means that said coating will undergo a distinct color change within about five minutes or less after said garment has been wetted with urine by a wearer of said garment.

* * * * *